US005679336A

United States Patent [19]

Ali et al.

[11] Patent Number: 5,679,336
[45] Date of Patent: Oct. 21, 1997

[54] ANTIBACTERIAL COMPOSITIONS

[75] Inventors: Yusuf Ali; Rajni Jani, both of Fort Worth, Tex.

[73] Assignee: Alcon Laboratories, Inc., Fort Worth, Tex.

[21] Appl. No.: 544,624

[22] Filed: Oct. 18, 1995

Related U.S. Application Data

[63] Continuation of Ser. No. 11,093, Jan. 29, 1993, abandoned, which is a continuation of Ser. No. 761,104, Sep. 17, 1991.

[51] Int. Cl.$^6$ .................................................. A61K 31/74
[52] U.S. Cl. ........................ 424/78.04; 514/254; 514/912
[58] Field of Search ................................ 514/236, 254, 514/300, 312, 912; 424/78.04

[56] References Cited

U.S. PATENT DOCUMENTS

| | | | |
|---|---|---|---|
| 4,146,719 | 3/1979 | Irikura | 544/363 |
| 4,292,317 | 9/1981 | Pesson | 424/250 |
| 4,382,892 | 5/1983 | Hayakawa et al. | 544/73 |
| 4,615,882 | 10/1986 | Stockel | 424/80 |
| 4,670,444 | 6/1987 | Grohe et al. | 514/300 |

*Primary Examiner*—Zohreh Fay
*Attorney, Agent, or Firm*—Sally Yeager

[57] ABSTRACT

Aqueous pharmaceutical compositions containing a synergistic combination of a quinolone and a polystyrene sulfonic acid polymer are described, wherein the compositions are clear solutions which are comfortable and have sustained release. Methods for use of the compositions are also disclosed. This type of formulation is particularly useful with ciprofloxacin-type quinolones by greatly increasing the solubility of these quinolones, making it feasible to have aqueous solutions containing such quinolones at or near physiological pH.

10 Claims, No Drawings

ANTIBACTERIAL COMPOSITIONS

This application is a continuation of application Ser. No. 08/011,093, filed Jan. 29, 1993, abandoned which is a continuation of application Ser. No. 07/761,104, filed Sept. 17, 1991.

BACKGROUND OF THE INVENTION

The present invention relates to pharmaceutical compositions comprising a synergistic combination of a quinolone and a polystyrene sulfonic acid polymer. In particular, the present invention relates to aqueous preparations containing a quinoline and a polystyrene sulfonic acid polymer, wherein the quinoline is solubilized by the polystyrene sulfonic acid polymer. These preparations are particularly well-suited for ophthalmic or otic use in the treatment of bacterial infections.

A number of quinolones have previously been used to treat bacterial infections through a variety of methods, including topical administration. Representative quinolones and antibacterial compositions thereof are: the norfloxacin-type quinolones, disclosed in U.S. Pat. Nos. 4,146,719 (Irikura) and 4,292,317 (Pesson); the ofloxacin-type quinolones, disclosed in U.S. Pat. No. 4,382,892 (Hayakaw, et al.); and the ciprofloxacin-type quinolones, disclosed in U.S. Pat. No. 4,670,444 (Grohe, et al.). The ciprofloxacin-type quinolones generally have a broader spectrum of anti-bacterial activity than either of the other types of quinolones listed above. Because of the poor solubility of these quinolones at physiological or higher pH, the ciprofloxacin-type quinolone formulations were developed at acidic pH and/or as suspensions; however, when these formulations were administered topically to the eye, they were uncomfortable.

SUMMARY OF THE INVENTION

The present invention provides aqueous pharmaceutical compositions and methods for the treatment of bacterial infections using these compositions. The compositions are particularly well-suited for ocular or otic use. The compositions of the present invention are formulated such that the solubility of quinolones at higher pH is increased by the use of an ionic polymer (namely, polystyrene sulfonic acid polymer) which binds the quinolone to the polymer. The binding between the polymer and the quinolone additionally provides both initial and continual comfort upon instillation to the eye, as there is less free drug to irritate the tissues of the eye. Another added benefit to the compositions of the present invention is that there is sustained release of the quinolone.

DETAILED DESCRIPTION OF THE INVENTION

The pharmaceutical compositions of the present invention contain a synergistic combination of a quinolone having antibacterial activity and a polystyrene sulfonic acid polymer, preferably at physiological or near-physiological pH. These compositions are especially useful in the eye, as the compositions are comfortable upon topical administration to the eye and provide sustained release of the quinolone.

The polystyrene sulfonic acid polymers (and their salts) which are used in the formulations of the present invention have the following formula:

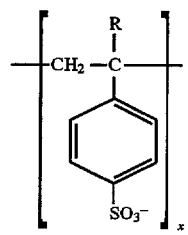

wherein,

R=H or $CH_3$; and

X=an integer such that the molecular weight of the polystyrene sulfonic acid polymer may vary from about 10,000 to 1.6 million.

In the preferred polystyrene sulfonic acid polymer of the above formula, R=H and the molecular weight is between about 500,000 to about 1,000,000, preferably about 600,000. The polystyrene sulfonic acid polymers are used in the formulas of the present invention at a concentration less than about 8.0 by weight (wt %), preferably less than about 5.0 wt %.

All quinolones having antibacterial activity and which are ophthalmically acceptable are useful in the compositions of the present invention, including, but not limited to the quinolones disclosed in U.S. Pat. Nos. 4,146,719 (Irikura), 4,292,317 (Pesson), 4,382,892 (HayaRawa, et al.), 4,670,444 (Grohe, et al.). The entire contents of these patents are hereby incorporated by reference herein.

The preferred quinolones useful in the compositions of the present invention are the type disclosed in U.S. Pat. No. 4,670,44 referenced above. The quinolones described therein are generally described as 7-amino-1-cyclopropyl-4-oxo-1,4-dihydro-quinoline- and -naphthyridine-3-carboxylic acids of the formula:

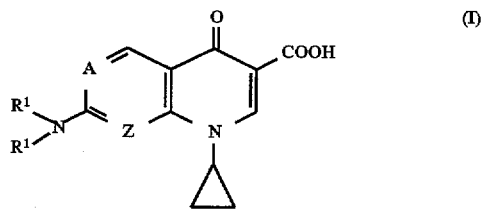

(I)

or a pharmaceutically acceptable acid addition salt or an alkali or alkaline earth metal salt thereof, in which A represents a nitrogen atom or $CR_3$, wherein $R_3$ denotes a hydrogen, a nitro group or a halogen atom, or a carboxamide or carboxyl group, and Z represents a nitrogen atom or C—H, and A and Z cannot simultaneously be nitrogen atoms, and $R_1$ and $R_2$ are identical or different and represent a hydrogen atom or a straight-chain or branched alkyl, alkenyl, or alkenyl radical which has up to 12 carbon atoms and is optionally substituted by radical(s) selected from hydroxyl, alkoxy, alkylmercapto or dialkylamino with 1 to 3 carbon atoms in each alkyl radical, alkoxycarbonyl with 1 to 4 carbon atoms in the alcohol part, and mono- or bi-cyclic carbocyclic aryl, or furthermore represents a cycloalkyl radical with 3 to 6 carbon atoms, or, together with the nitrogen atom which they substituted or together with a further hetero-atom selected from the group consisting of N, O and S form a 3-membered to 7-membered ring which can be substituted by radical (s) selected from alkyl or alkenyl with 1 to 6 carbon atoms, hydroxyl, alkoxy or alkylmercapto with 1 to 3 carbon atoms, alkoxy carbonyl with 1 to 4 carbon atoms in the alcohol part, and mono- or bi-cyclic carbocyclic aryl.

More preferred are the 1-cyclopropyl-6-fluoro-1,4-dihydro-4-oxo-7-piperazino-quinoline-3-carboxylic acids of the formula:

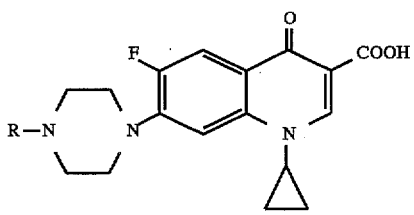

(II)

or salts and/or hydrates thereof, in which R denotes hydrogen, methyl, ethyl or β-hydroxyethyl.

Most preferred is ciprofloxacin, which has the following structure:

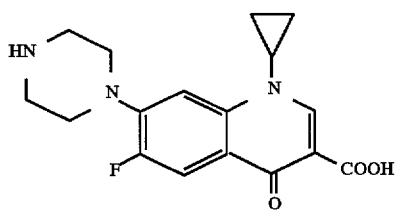

The chemical name for ciprofloxacin is 1-cyclopropyl-6-fluoro-1,4-dihydro-4-oxo-7-(1-piperazinyl)-3-quinoline carboxylic acid.

Methods of preparation for the preferred quinolones are described in U.S. Pat. No. 4,670,444. The quinolone component of the pharmaceutical compositions of the present invention generally contain less than about 1.0 wt % of the total composition, preferably between about 0.1 wt % to about 0.75 wt %. The most preferred quinolone concentration is between about 0.2 to about 0.4 wt %.

The compositions of the present invention are prepared by combining the quinolone with polystyrene sulfonic acid polymer in aqueous media and adjusting the pH, if necessary. The compositions of the present invention may also include one or more ingredients conventionally found in ophthalmic or otic formulations, such as preservatives (e.g., benzalkonium chloride or thimerosal), viscosity-imparting agents (e.g., polyvinyl alcohol or hydroxyprovomethylcellulose) and tonicity agents (e.g., sodium chloride or mannitol). The compositions will also normally include buffering agents, such as phosphates and citrates, to maintain the pH within the range of physiological pH (pH between 6.0 and 7.5) and tonicity agents, such as mannitol. Hydrochloric acid or sodium hydroxide will typically be used to adjust the pH of the resultant composition.

The following example is presented to illustrate further certain preferred embodiments of the present invention and should not be interpreted as limiting the scope of the invention in any way.

EXAMPLE 1

The following represents a preferred embodiment of the compositions of the present invention.

| Ingredient | Amount (wt %) |
|---|---|
| Ciprofloxacin HCl, Monohydrate | 0.35* |
| PSSA | 50 ml** |
| Mannitol | 3.75 |
| Benzalkonium chloride | 0.01 |
| NaOH and/or HCl | to pH 7.0 |
| Purified Water | Q.S. |

*Equivalent to 0.3% as base
**2% PSSA solution in water

The 2% PSSA solution was filtered through a 0.6 micron filter, 50 milliliters (ml) of the filtered solution added to a first beaker, and the contents stirred. To a second beaker were added 15 ml of water and the ciprofloxacin and the mixture stirred until the ciprofloxacin was completely dissolved, at which point the mannitol and benzalkonium chloride were added and the contents stirred again, until a homogeneous solution was achieved. Then the contents of the second beaker were slowly added to the contents of the first beaker, while stirring. The pH was then adjusted to pH 7.0 using NaOH and water was added to bring the volume of the final solution to 100 ml.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. An aqueous pharmaceutical composition comprising: a polystyrene sulfonic acid polymer having the formula

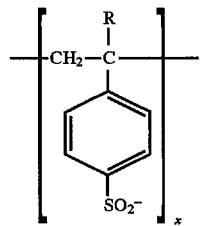

wherein: R=H or $CH_3$; and X=an integer such that the molecular weight of the polystyrene sulfonic acid polymer may vary from about 10,000 to 1.6 million in an amount capable of solubilizing ciprofloxacin at physiological pH and a therapeutically effective amount of ciprofloxacin.

2. The composition of claim 1 wherein the 1-cyclopropyl-6-fluoro-1,4-dihydro-4-oxo-7-(1-piprazinyl)-3-quinoline carboxylic acid is present at a concentration less than or equal to about 1.0 wt %.

3. The composition of claim 2 wherein the 1-cyclopropyl-6-fluoro-1,4-dihydro-4-oxo-7-(1-piprazinyl)-3-quinoline carboxylic acid is present at a concentration between about 0.1 wt % and 0.75 wt %.

4. The composition of claim 3 wherein the 1-cyclopropyl-6-fluoro-1,4-dihydro-4-oxo-7-(1-piprazinyl)-3-quinoline carboxylic acid is present at a concentration between about 0.2 wt % and 0.4 wt %.

5. The composition of claim 4 wherein the 1-cyclopropyl-6-fluoro-4-dihydro-4-oxo-7-(1-piprazinyl)-3-quinoline carboxylic acid is present at a concentration of about 0.3 wt %.

6. A method for the treatment of ophthalmic bacterial infections which comprises the topical administration of an aqueous pharmaceutical composition comprising a polystyrene sulfonic acid polymer having the formula

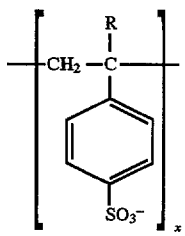

wherein: R=H or CH$_3$; and X=an integer such that the molecular weight of the polystyrene sulfonic acid polymer may vary from about 10,000 to 1.6 million in an amount capable of solubilizing ciprofloxacin at physiological pH and a therapeutically effective amount of ciprofloxacin.

7. The method of claim 6 wherein the 1-cyclopropyl-6-fluoro-1,4-dihydro-4-oxo-7-(1-piprazinyl)-3-quinoline carboxylic acid is present at a concentration less than or equal to about 1.0 wt %.

8. The method of claim 7 wherein the 1-cyclopropyl-6-fluoro-1,4-dihydro-4-oxo-7-(1-piprazinyl)-3-quinoline carboxylic acid is present at a concentration between about 0.1 wt % to about 0.75 wt %.

9. The composition of claim 8 wherein the 1-cyclopropyl-6-fluoro-4-dihydro-4-oxo-7-(1-piprazinyl)-3-quinoline carboxylic acid is present at a concentration between about 0.2 wt % and 0.4 wt %.

10. The composition of claim 9 wherein the 1-cyclopropyl-6-fluoro-1,4-dihydro-4-oxo-7-(1-piprazinyl)-3-quinoline carboxylic acid is present at a concentration of about 0.3 wt %.

* * * * *

UNITED STATES PATENT AND TRADEMARK OFFICE
CERTIFICATE OF CORRECTION

PATENT NO. : 5,679,336
DATED : October 21, 1997
INVENTOR(S) : Ali, et al.

It is certified that error appears in the above-identified patent and that said Letters Patent is hereby corrected as shown below:

Claim 1, column 4, line 44, change "$SO_2^-$" to $SO_3^-$.

Signed and Sealed this

Tenth Day of March, 1998

Attest:

BRUCE LEHMAN

*Attesting Officer*    *Commissioner of Patents and Trademarks*